United States Patent
Ben-Kiki et al.

(10) Patent No.: US 10,813,584 B2
(45) Date of Patent: Oct. 27, 2020

(54) ASSESSING ADHERENCE FIDELITY TO BEHAVIORAL INTERVENTIONS USING INTERACTIVITY AND NATURAL LANGUAGE PROCESSING

(71) Applicant: Happify, Inc., New York, NY (US)

(72) Inventors: Tomer Ben-Kiki, New York, NY (US); Ran Zilca, Ra'anana (IL)

(73) Assignee: HAPPIFY, INC., New York, NY (US)

(*) Notice: Subject to any disclaimer, the term of this patent is extended or adjusted under 35 U.S.C. 154(b) by 0 days.

(21) Appl. No.: 16/032,344

(22) Filed: Jul. 11, 2018

(65) Prior Publication Data

US 2018/0317840 A1 Nov. 8, 2018

Related U.S. Application Data

(63) Continuation-in-part of application No. 15/974,978, filed on May 9, 2018, and a continuation-in-part of
(Continued)

(51) Int. Cl.
*A61B 5/00* (2006.01)
*A61M 21/02* (2006.01)
(Continued)

(52) U.S. Cl.
CPC ............ *A61B 5/4833* (2013.01); *A61B 5/165* (2013.01); *A61B 5/486* (2013.01); *A61B 5/7425* (2013.01);
(Continued)

(58) Field of Classification Search
CPC .......................... A61B 5/4833; A61B 5/4836
(Continued)

(56) References Cited

U.S. PATENT DOCUMENTS 5,722,418 A    3/1998   Bro
6,293,904 B1   9/2001   Blazey
(Continued)

FOREIGN PATENT DOCUMENTS

CN   101799849 A    8/2010
CN   103400054 A    11/2013
(Continued)

OTHER PUBLICATIONS

Beun et al., "Improving Adherence in Automated e-Coaching", International Conference on Persuasive Technology, Persuasive 2016: Persuasive Technology pp. 276-287. (Year: 2016).*
(Continued)

*Primary Examiner* — Backhean Tiv
*Assistant Examiner* — Jonathan A Sparks
(74) *Attorney, Agent, or Firm* — Harness, Dickey & Pierce, P.L.C.

(57) ABSTRACT

A computer system apparatus and a method carried out by such apparatus for interacting with a user via a behavior intervention designed to cause an increase in emotional well-being of the user. The behavior intervention has a plurality of conditions to be satisfied. The process includes receiving input data from the user during the behavior intervention, performing, on at least a portion of the received input data having text, semantic analysis to identify terms that satisfy the plurality of conditions and assessing, based on an amount of completeness of satisfying the plurality of conditions, a level of adherence to the behavior intervention. When one or more of the plurality of conditions are determined not as satisfied, the process includes generating a prompt designed to elicit, from the user, a response specific to satisfying the missing conditions.

25 Claims, 4 Drawing Sheets

Related U.S. Application Data application No. 14/990,380, filed on Jan. 7, 2016, and a continuation-in-part of application No. 14/284,229, filed on May 21, 2014, now abandoned.

(60) Provisional application No. 62/656,231, filed on Apr. 11, 2018, provisional application No. 62/533,423, filed on Jul. 17, 2017, provisional application No. 62/101,315, filed on Jan. 8, 2015, provisional application No. 61/825,742, filed on May 21, 2013.

(51) Int. Cl.

| | | |
|---|---|---|
| *G06K 9/00* | (2006.01) | |
| *A61M 21/00* | (2006.01) | |
| *A61B 5/16* | (2006.01) | |
| *G10L 15/22* | (2006.01) | |
| *G10L 25/63* | (2013.01) | |
| *G06F 40/30* | (2020.01) | |

(52) U.S. Cl.
CPC ............ *A61M 21/02* (2013.01); *G06F 40/30* (2020.01); *G06K 9/00442* (2013.01); *G10L 15/22* (2013.01); *G10L 25/63* (2013.01); *A61B 5/4836* (2013.01); *A61M 2021/005* (2013.01); *A61M 2021/0027* (2013.01); *A61M 2205/3303* (2013.01); *A61M 2205/3375* (2013.01); *A61M 2205/3553* (2013.01); *A61M 2205/3584* (2013.01); *A61M 2205/502* (2013.01); *A61M 2205/505* (2013.01); *A61M 2205/52* (2013.01); *A61M 2230/50* (2013.01); *A61M 2230/63* (2013.01); *G06K 2009/00489* (2013.01); *G10L 2015/227* (2013.01)

(58) Field of Classification Search
USPC ......................................................... 709/204
See application file for complete search history.

(56) References Cited

U.S. PATENT DOCUMENTS

| | | | |
|---|---|---|---|
| 6,728,679 B1 | 4/2004 | Strubbe et al. | |
| 7,644,060 B2 | 1/2010 | Kadri | |
| 8,577,671 B1 | 11/2013 | Barve et al. | |
| 2007/0143281 A1 | 6/2007 | Smirin et al. | |
| 2009/0037470 A1 | 2/2009 | Schmidt | |
| 2009/0119234 A1 | 5/2009 | Pinckney et al. | |
| 2009/0171902 A1 | 7/2009 | MacLaurin | |
| 2010/0218118 A1 | 8/2010 | Bronkema | |
| 2011/0125844 A1 | 5/2011 | Collier et al. | |
| 2011/0183305 A1 | 7/2011 | Orbach | |
| 2012/0095862 A1 | 4/2012 | Schiff et al. | |
| 2012/0246102 A1 | 9/2012 | Sudharsan | |
| 2012/0315613 A1 | 12/2012 | Shade et al. | |
| 2013/0101970 A1 | 4/2013 | Mascarenhas | |
| 2014/0157171 A1* | 6/2014 | Brust ................... | G06F 3/0481 715/771 |
| 2014/0212853 A1* | 7/2014 | Divakaran ............ | G09B 19/00 434/236 |
| 2014/0223462 A1 | 8/2014 | Aimone | |
| 2014/0276244 A1 | 9/2014 | Kamyar | |
| 2015/0140527 A1 | 5/2015 | Gilad-Barach et al. | |
| 2015/0199010 A1 | 7/2015 | Coleman et al. | |
| 2015/0297109 A1 | 10/2015 | Garten et al. | |
| 2015/0339363 A1 | 11/2015 | Moldoveanu | |
| 2015/0348569 A1 | 12/2015 | Allam et al. | |
| 2015/0371663 A1 | 12/2015 | Gustafson et al. | |
| 2016/0055236 A1 | 2/2016 | Frank et al. | |
| 2016/0203729 A1 | 7/2016 | Zilca | |
| 2017/0125008 A1 | 5/2017 | Maisonnier et al. | |

FOREIGN PATENT DOCUMENTS

| | | | |
|---|---|---|---|
| WO | | 0122384 A1 | 3/2001 |
| WO | WO-2010144766 A1 | | 12/2010 |
| WO | | 2012094516 A1 | 7/2012 |
| WO | | 2013059290 A1 | 4/2013 |

OTHER PUBLICATIONS

Ciaramicoli, "What is Empathic CBT", <https://web.archive.org/web/20161014010605/http://www.balanceyoursuccess.com/what-is-empathic-cbt/> (Year: 2016).*
European Search Report dated Nov. 23, 2016, that issued in European Patent Application No. 14801490.5.
International Search Report dated Nov. 6, 2014, that issued in the corresponding European Patent Application No. PCT/US2014/039022.
Greenolive: an Open Platform for Wellness Management Ecosystem, by Zeng et al., 2010 (Year: 2010).
The International Search Report of International Application No. PCT/US2018/041603 dated Nov. 8, 2018.
The International Search Report of International Application No. PCT/US2018/042272 dated Nov. 29, 2018.
U.S. Appl. No. 16/600,903, filed Oct. 14, 2019, Tomer Ben-Kiki.
U.S. Appl. No. 14/990,380, filed Jan. 7, 2016, Ran Zilca.
U.S. Appl. No. 15/974,978, filed May 9, 2018, Tomer Ben-Kiki.
U.S. Appl. No. 16/059,498, filed Aug. 9, 2018, Tomer Ben-Kiki.
European Examination Report for Application No. 14801490.5 dated Oct. 22, 2019.
International Search Report and Written Opinion for International Application No. PCT/US2019/036972 dated Sep. 23, 2019.
International Preliminary Report on Patentability for International Application No. PCT/US2018/041603 dated Jan. 21, 2020.
International Preliminary Report on Patentability for International Application No. PCT/US2018/042272 dated Jan. 30, 2020.
Canadian Office Action dated Apr. 16, 2019 for corresponding Canadian Application 2,949,605 filed Nov. 18, 2016 (4 pages).
Canadian Office Action dated Apr. 30, 2020 for corresponding Canadian Application 2949605, filed Nov. 18, 2016 (9 pages).
Chinese Office Action dated Aug. 14, 2018 in corresponding Chinese Application 201480041214.1 filed Jan. 20, 2016 (5 pages).
Chinese Office Action dated Aug. 24, 2017 in corresponding Chinese Application 201480041214.1 filed Jan. 20, 2016 (7 pages).
Chinese Office Action dated Mar. 14, 2019 in corresponding Chinese Application 201480041214.1 filed Jan. 20, 2016 (10 pages).
Chinese Office Action dated Sep. 29, 2019 in corresponding Chinese Application 201480041214.1 filed Jan. 20, 2016 (8 pages).

* cited by examiner

ASSESSING ADHERENCE FIDELITY TO BEHAVIORAL INTERVENTIONS USING INTERACTIVITY AND NATURAL LANGUAGE PROCESSING

CROSS-REFERENCE TO RELATED APPLICATIONS

This application claims priority under 35 U.S.C. § 119(e) to U.S. Provisional Application Ser. No. 62/533,423, filed on Jul. 17, 2017. This application is also a continuation-in-part of U.S. Non-Provisional application Ser. No. 14/284,229, filed on May 21, 2014, which claims priority under 35 U.S.C. § 119(e) to U.S. Provisional Application Ser. No. 61/825,742, filed on May 21, 2013. This application is also a continuation-in-part of U.S. Non-Provisional application Ser. No. 14/990,380, filed on Jan. 7, 2016, which claims priority under 35 U.S.C. § 119(e) to U.S. Provisional Application Ser. No. 62/101,315, filed on Jan. 8, 2015. This application is also a continuation-in-part of U.S. Non-Provisional application Ser. No. 15/974,978, filed on May 9, 2018, which claims priority under 35 U.S.C. § 119(e) to U.S. Provisional Application Ser. No. 62/656,231, filed on Apr. 11, 2018. The entire contents of each above-noted application is herein incorporated by reference in their entirety.

FIELD OF INVENTION

The present invention is directed to a computing system, and a process carried out by such system, for assessing a degree to which a user is adhering to behavior interventions and for responding in a way to guide the user toward maximized adherence, and thus, toward increased efficacy of the behavior interventions.

BACKGROUND

Behavioral interventions often involve providing a user/patient with a set of instructions and collecting a text/verbal response. Such interventions have an intended implementation aimed at activating certain psychological mechanisms. When users adhere to the instructions in a way that is faithful to the intended implementation, the intervention is expected to be efficacious. However, when users do not adhere, or only adhere partly to the intended implementation, the intervention may not be as efficacious, and an increased well-being may not be achieved.

For example, a user who writes about negative events when the intended implementation is to write about positive events, is not expected to benefit much from the activity because the psychological mechanism of shifting focus to the positive will not be activated. Another example is a user who is asked to write empathetically about another person, but writes about themselves instead. Such a user is not following the intended implementation of developing empathetic skills, and the psychological mechanism of connecting with others is not activated, resulting in decreased efficacy of the intervention, or even worse, resulting in decreased well-being of the user which is clearly the opposite of the intended outcome of the intervention.

In human-to-human conversation (e.g., in psychotherapy of personal coaching), it is possible to assess the degree to which a person is adhering to an intended implementation and converse with them in a way that will maximize adherence and therefore increase efficacy. In contrast, in software-implemented behavioral interventions, computer systems do not normally have a way of assessing such adherence fidelity. Furthermore, such computer systems have no mechanism for directing the interaction with users in a way that will maximize the expected efficacy by maximizing adherence.

OBJECTS AND SUMMARY OF THE INVENTION

In view of the foregoing, it is an object of the present invention to provide a computing system/method for assessing a degree to which a user is adhering to behavior interventions and for responding in a way to guide the user toward maximized adherence. It is another object of the present invention to provide a computing system/method for, by perfecting adherence to intended implementations of behavior interventions, achieving maximized increase in well-being that is possible from the behavior interventions.

In accordance with an embodiment of the present invention, a computing system for interacting with a user is provided, in which the computing system commences, with a user, a behavior intervention designed to cause an increase in emotional well-being of the user, the behavior intervention having a plurality of conditions to be satisfied, receives, via at least one sensor, input data from the user during the behavior intervention, performs, on at least a portion of the received input data having text, semantic analysis to identify terms that satisfy the plurality of conditions, and assesses, based on an amount of completeness of satisfying the plurality of conditions, a level of adherence to the behavior intervention. The computing system further generates a prompt designed to elicit, from the user, a response specific to satisfying one or more of the plurality of conditions not satisfied.

As an aspect of this embodiment, the computing system receives, via the at least one sensor, input data from the user during the behavior intervention to assess a psychological state of the user while simultaneously assessing the level of adherence to the behavior intervention.

As another aspect, the computing system assesses, at a plurality of points in time during the behavior intervention, a respective level of adherence to the behavior intervention at the respective point in time.

As a feature of this aspect, the computing system generates, at each of the plurality of points in time, a respective fidelity report containing the respective level of adherence to the behavior intervention assessed at the respective point in time during the behavior intervention.

As another feature of this aspect, the computing system generates, at the end of the behavior intervention, an overall fidelity report for the behavior intervention based on a plurality of fidelity reports.

As a further feature of this aspect, the computing system further comprises a display, and displays on the display, at least one of the fidelity report and the overall fidelity report for viewing by the user. The displaying of the at least one of the fidelity report and the overall fidelity report further enables the user to understand reasons behind efficacy of the behavior intervention.

As another aspect, the behavior intervention further includes a programmed branching logic for responding to the received input data. The computing system, upon a determination that one or more of the plurality of conditions have yet to be satisfied and generating the prompt designed to elicit, from the user, the response specific to satisfying the one or more of the plurality of conditions not satisfied, assigns a priority to the generated prompt such that the generated prompt overrides the programmed branching logic for responding to the received input data.

As a further aspect, the behavior intervention is designed to cause an increase in level of happiness of the user.

As a further aspect, the behavior intervention is an activity from a pluralities of activities belonging to a Happiness track selected by the user from a plurality of selectable Happiness tracks, wherein each Happiness track is a distinct course of program designed to cause an increase in level of happiness of the user.

As yet another aspect, the behavior intervention is designed to cause a change in one or more of the user's behaviors.

As yet a further aspect, the received input data comprises at least one of verbal and text data from the user.

As still yet another aspect, the semantic analysis includes pre-training a natural language classifier based on a database of user input data and the classifier creating one or more labels to be associated with each of the plurality of conditions.

As a feature of this aspect, the semantic analysis includes determining whether the terms identified in the received input data correspond to the one or more labels.

In accordance with another embodiment of the present invention, a method of interacting with a user by a computing system is provided, in which the inventive method comprises commencing, with the user, a behavior intervention designed to cause an increase in emotional well-being of the user, the behavior intervention having a plurality of conditions to be satisfied, receiving, via at least one sensor, input data from the user during the behavior intervention, performing, on at least a portion of the received input data having text, semantic analysis to identify terms that satisfy the plurality of conditions, assessing, based on an amount of completeness of satisfying the plurality of conditions, a level of adherence to the behavior intervention, and generating a prompt designed to elicit, from the user, a response specific to satisfying one or more of the plurality of conditions not satisfied.

As an aspect of this embodiment, the method further comprises receiving, via the at least one sensor, input data from the user during the behavior intervention to assess a psychological state of the user while simultaneously assessing the level of adherence to the behavior intervention.

As another aspect, the method further comprises assessing, at a plurality of points in time during the behavior intervention, a respective level of adherence to the behavior intervention at the respective point in time.

As a feature of this aspect, the method further comprises generating, at each of the plurality of points in time, a respective fidelity report containing the respective level of adherence to the behavior intervention assessed at the respective point in time during the behavior intervention.

As another feature of this aspect, the method further comprises generating, at the end of the behavior intervention, an overall fidelity report for the behavior intervention based on a plurality of fidelity reports.

As a further feature of this aspect, the method further comprises displaying, on a display, at least one of the fidelity report and the overall fidelity report for viewing by the user. The displaying of the at least one of the fidelity report and the overall fidelity report further enables the user to understand reasons behind efficiency of the behavior intervention.

As another aspect, the behavior intervention further includes a programmed branching logic for responding to the received input data. The method further comprises, upon a determination that one or more of the plurality of conditions have yet to be satisfied, and generating the prompt designed to elicit, from the user, the response specific to satisfying the one or more of the plurality of conditions not satisfied, assigning a priority to the generated prompt such that the generated prompt overrides the programmed branching logic for responding to the received input data.

As yet another aspect, the behavior intervention is designed to cause an increase in level of happiness of the user.

As yet a further aspect, the behavior intervention is an activity from a plurality of activities belonging to a Happiness track selected by the user from a plurality of selectable Happiness tracks, wherein each Happiness track is a distinct course of program designed to cause an increase in level of happiness of the user.

As yet another aspect, the behavior intervention is designed to cause a change in one or more of the user's behaviors.

As still yet another aspect, the received input data comprises at least one of verbal and text data from the user.

As still yet a further aspect, the semantic analysis includes pre-training a natural language classifier based on a database of user input data and the classifier creating one or more labels to be associated with each of the plurality of conditions.

As a feature of this aspect, the semantic analysis further includes determining whether the terms identified in the received input data correspond to the one or more labels.

In accordance with a further embodiment of the present invention, a computing system for interacting with a user is provided, in which the computing system commences, with a user, an empathy behavior intervention designed to cause an increase in expressing empathy by the user, the empathy behavior intervention having a plurality of conditions to be satisfied, receives, via at least one sensor, input data from the user during the behavior intervention, performs, on at least a portion of the received input data having text, semantic analysis to identify terms that satisfy the plurality of conditions, and assesses, based on an amount of completeness of satisfying the plurality of conditions, a level of adherence to the behavior intervention. The computing system further generates a prompt designed to elicit, from the user, a response specific to satisfying one or more of the plurality of conditions not satisfied.

These and other objects, advantages, aspects and features of the present invention are as described below and/or appreciated and well understood by those of ordinary skill in the art. Although specific advantages have been enumerated above, various embodiments may include some, none, or all of the enumerated advantages and other technical advantages may become readily apparent to one of ordinary skill in the art after review of the following figures and description.

DETAILED DESCRIPTION

Figure 1:
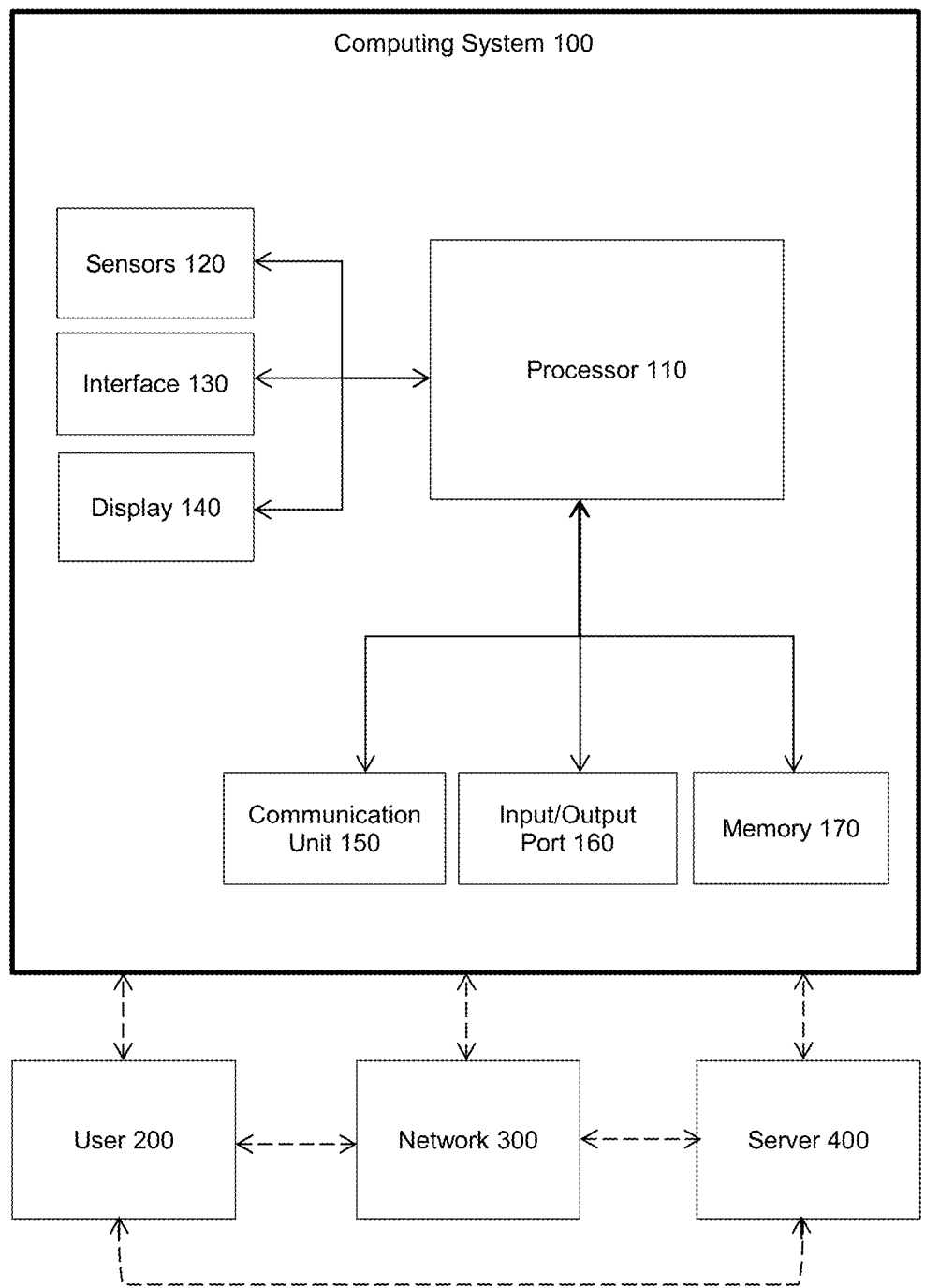
FIG. 1 is a block diagram of an exemplary computing system in accordance with the present invention.

The present invention is directed to a computing system, as well as a method employed by a technological device, that provides an environment for interacting with a (human) user via behavioral interventions, and in the midst of such interaction, assessing a degree to which the user is adhering to the provided behavior interventions. The computing system makes assessment of adherence fidelity at key steps of the intervention using a plurality of sensors and analytic techniques, and ultimately, formulates an individualized and/or an overall fidelity report that may serve as a basis for understanding how and why certain behavior interventions work or don't work.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

The term a "behavioral intervention," or just simply, an "intervention" as used herein is intended to be construed broadly, and as such, the term may include a variety of interventions that are designed specifically to increase physical and/or emotional well-being of a user/patient. In accordance with the present invention, an "intervention" may simply be an activity, based on prior evidence-based research, showing that when a person engages with the activity (as intended), the person benefits in terms of his or her psychological and/or physical well-being. In accordance with the present invention, a computing system "provides" a user with an intervention. Generally, this terminology is intended to mean that the computing system loads an intervention, i.e., a stored executable program or a mobile application and commences and/or engages in the user in a set of activities. An intervention is generally comprised of a set of pre-arranged activities or conversations or tasks to be carried out or otherwise performed either by the user or between the user and a coach (or a virtual coach). An intervention also generally has a purpose of activating certain mental or physical mechanisms within the user's mind and/or body, by bringing out certain emotional reactions from the user. As such, an intervention generally comes with an intended implementation, that is, a specific method or approach intended by a creator of such intervention for the set of pre-arranged activities to be carried out in order to most efficiently achieve the underlying purpose behind the intervention. The intended implementation may come in the forms of criteria, conditions, requirements, or factors that are each designed to be met by the user by performing a specific act or speaking a specific word. Accordingly, the most ideal and efficacious way to advance an intervention is for the user to stay faithful to the intended implementation through the course of the intervention.

In accordance with various embodiments of the present invention as described herein, an intervention may be used to train a user to develop certain skills or to modify certain habitual behaviors to address an issue that the user is facing in life. For example, such interventions may include behavioral-change interventions, positive interventions, and clinical interventions (such as Cognitive Behavioral Therapy (CBT), Acceptance and Commitment Therapy (ACT), Solution Focused Therapy SFT), Behavior Activation (BA), or Behavior Change Interventions). Further in accordance with the present invention, such interventions are of variable lengths, since the computing system, as will also be described herein, dynamically decides how to continue the interaction at each turn of the intervention based on an assessment of the user's adherence to the intended implementation of the intervention.

Referring now to the drawings in which like numerals represent the same or similar elements, and initially to FIG. 1 thereof, a computing system 100 configured in accordance with the present invention is illustratively shown in accordance with one embodiment. The computing system 100 includes one or more processors 110 that processes various input data and stored data and controls operations of other components within the computing system 100 to enable the herein described "behavior intervention" between a user or users 200 and the computing system 100. As will be further described, the processor 110 processes data by performing numerous mathematical algorithms and analytical computations. The processor 110 may also be a plurality of processing units that each carries out respective mathematical algorithm and/or analytical computation. In some embodiments, the processor 110 is enhanced by artificial intelligence.

The computing system 100 further includes a plurality of sensors 120. The plurality of sensors 120 may comprise a speaker/microphone, a still image camera, a moving image camera, a biometric sensor, etc. Each of the sensors 120 is configured to obtain user input data and may further comprise one or more respective processing units to process the obtained input data in conjunction with the processor 110. The computing system 100 further includes an interface 130 to allow the user 200 to operate the computing system and a display 140 to present information to the user 200. In some embodiments, the interface 130 and the display 140 may come as one unit such as a touch screen display.

The computing system 100 further includes a communication unit/device 150, an input/output port 160 and a memory 170. The communication unit/device 150 allows the computing system 100 to communicate with the user's other electronic devices or with additional sensors within a vicinity of the user 200 over a network 300. The network 300 may include wireless communications, wired communications, etc. The network 300 may include the Internet, a wide area or local area network, etc. The computing system 100 may use the I/O port 160 for inputting and outputting data. The computing system 100 further includes the memory 170 which stores programs and applications. The memory 170 may store a database of interventions or may locally store interventions retrieved from a server 400 having thereon a database of interventions.

The computing device 100, as well as the user's other electronic devices or the additional sensors, may be part of or otherwise be connected to the network 300 and coupled to a server or a service provider 400. The broken lines in FIG. 1 signify that the user 200, the network 300, the server 400 and the computing system 100 may be connected to any one or more of the user 200, the network 300, the server 400 or the computing system 100, either directly, indirectly, or remotely over a communication path. One or more of the computing system 100, the network 300 and the server 400 may be located on one computer, distributed over multiple computers, or be partly or wholly Internet-based.

In accordance with certain exemplary embodiments of the present invention, the computing system embodies a positive psychology service referred to herein as "Happify." Happify is a novel, science-based online service for engaging, learning and training the skills of happiness. Happify is based on a framework developed by psychologists and researchers in a collection of therapeutic disciplines such as CBT, Mindfulness, Positive Psychology etc., and assists users in the development of certain skills related to being happy, for example, Savor, Thank, Aspire, Give and Empathize (or S.T.A.G.E.™). In certain embodiments, each skill is developed using various activities, ordered in increasing skill level, that gradually unlock as the user progresses in building that skill. With Happify, a user selects a "track" that contains sets of activities that are designed to address a specific life situation or goal.

The Happify system may be implemented on a user's mobile electronic device, such as a smartphone or tablet, or may be implemented on the user's personal computer (PC). Happify may be embodied within a mobile application, an executable software program, or another suitable form. For instance, a user may download and install a mobile application that provides the Happify service. The user, via the mobile application, selects a Happiness track and is provided with sets of activities that are designed to improve the user's happiness level in accordance with the selected track.

Further details of the Happify system and operations of the Happify system are set forth in U.S. patent application Ser. No. 14/284,229, entitled "SYSTEMS AND METHODS FOR PROVIDING ON-LINE SERVICES," U.S. patent application Ser. No. 14/990,380, entitled "DYNAMIC INTERACTION SYSTEM AND METHOD," and U.S. patent application Ser. No. 15/974,978, entitled "SYSTEMS AND METHODS FOR DYNAMIC USER INTERACTION FOR IMPROVING HAPPINESS," and the entire contents of each of these applications is incorporated herein by reference. For the sake of brevity, further details of the Happify system/service are not provided herein (except as otherwise described herein).

In accordance with the present invention, an exemplary computing system embodying the Happify system provides to a user a set of activities as part of a selected Happiness track. These "activities" may also be referred to herein as another type of "intervention." Each activity has its own intended implementation, purpose, and science-based foundation in developing skills related to increasing a happiness level of a user, and as each activity is provided to and progressed by the user, the computing system employs various computer-specific mechanisms to track and assess the user's adherence at each turn of the activity.

Figure 2:
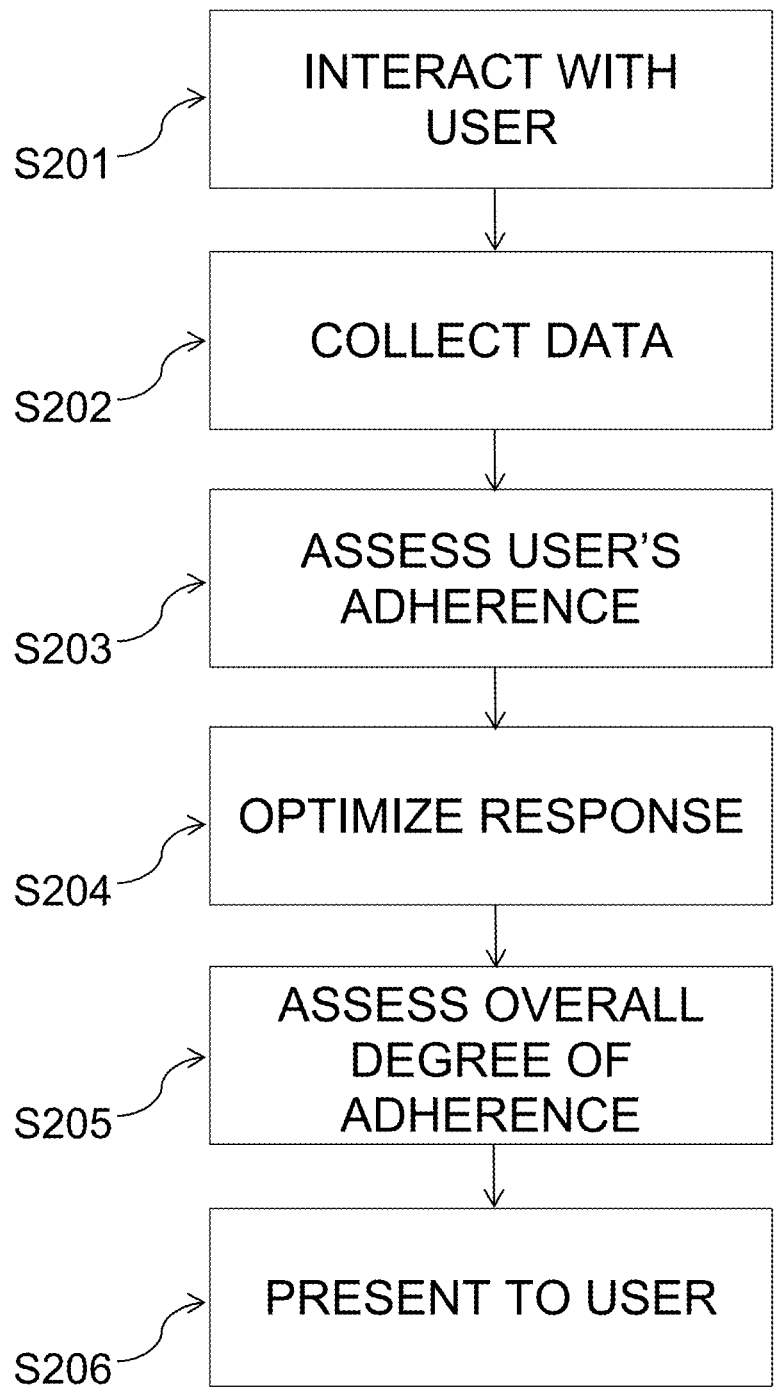
FIG. 2 is an exemplary flow chart showing an overview of steps carried out by an exemplary embodiment of the present invention.

An overview of the steps carried out by an exemplary computing system in accordance with the present invention is shown in FIG. 2.

In accordance with the present invention, Step S201 entails interacting with a user in an iterative way (i.e., engaging in a conversation either via text or via voice). For example, an iterative interaction initiated by the computing system may comprise providing a user with a prompt, receiving input data from the user, providing a follow-up prompt to the user, receiving further input data from the user, etc.

Step S202 entails collecting data from an array of sensors that extract features from the user's responses at key steps of the interaction. For example, the computing system may be in communication (e.g., wired or wireless) with one or more devices configured to collect user information such as a camera, speaker, microphone, heat sensor, motion sensor, fingerprint detector, keyboard, etc. Such devices may encompass various structures and/or functionalities, and may further include one or more processors to perform various natural language understanding tools.

Step S203 entails, at the key steps of the interaction, using the collected data to assess a fidelity of the user's adherence to one or more intended implementation of a provided activity. For example, any given behavior intervention may comprise a plurality of components, conditions and/or criteria that are required in order to consider the intervention as being complete. The computing system performs analyses that will allow the computing system to recognize, at key steps of the interaction, whether or how certain of the components, conditions and/or criteria are being progressed.

Step S204 entails using this assessment, determining an optimized response to the user at each of the key steps of the interaction/conversation to guide the interaction toward maximized or improved adherence. For example, while the given interaction may comprise a predetermined sequence or course of action, the computing system, based on the assessment, may intervene or deviate from the predetermined sequence by, for example, asking different questions using programmed branching logic, for the purpose of guiding the user toward maximized or improved adherence.

Step S205 entails, at the end of the interaction, assessing an overall degree of adherence to the intended implementation of the intervention.

Finally, step S206 entails presenting to the user the degree of overall adherence of each intervention as a score and using the degree of overall adherence as an indication of progress through a program of behavioral interventions.

Additional details as to each of the above steps above will be discussed in greater depth herein.

Initially, as described above, the computing system in accordance with the present invention provides a behavior intervention to a user by engaging in an iterative interaction with the user. As described herein, such interaction comprises starting a conversation with the user, assessing the current psychological state of the user, providing an activity or a task to be performed by the user, etc. In accordance with the present invention, the computing system receives input data from the user, either directly from the user or indirectly via one or more sensors, analyzes the input data and responds back to the user. This iterative interaction continues until, for example, a desired outcome is achieved. In one or more embodiments, the computing system may be equipped with particular software that enables the computing system to dynamically interact with the user in response to ongoing input data or to emotionally (e.g., empathetically) interact with the user for various reasons.

In accordance with the embodiments of the present invention, the computing system is equipped with a novel ability to assess, whether simultaneously, sequentially, or independently, the user's adherence fidelity at various steps during an intervention. For example, the computing system in one embodiment may collect and analyze user input text/verbal data to continually update the user's psychological state while simultaneously performing analysis on the collected input text/verbal data to assess the user's adherence fidelity each time input data is received. In another embodiment, the computing system assesses the user's adherence fidelity before or after other analyses are performed on the input text/verbal data for each input data. In a further embodiment, the assessment of adherence fidelity may be performed independently at each step of the intervention or at a predetermined interval of time throughout the course of the intervention.

As described herein, the computing system employs sensors that are configured to collect and analyze user input data. The term "sensor" as used herein includes a computer keyboard or other type of computer data entry device, such as a touch screen, a mouse, a microphone, etc., and any of the other sensors or other devices disclosed herein or otherwise known in the art through which a user is able to, either actively or passively, provide information to the system. Various types of sensors may be employed to collect auditory or visual data, or the user may directly type or write input data that are received by the computing system. The sensors not only collect data, but also perform analyses, and below are exemplary lists of analytic techniques carried out by the sensors for the purposes of extracting information from input data and, based on such information, assessing the user's adherence level to the intended implementations of the behavior interventions.

I. Named Entity Recognition

One or more of the sensors as described herein are equipped with processing units to perform "Named Entity Recognition" analysis, which is the ability to identify entities in a body of text, and refer to the identified entities in a unified, canonicalized fashion, regardless of specific wording. For example, the phrases "Facebook founder", "Mark Zuckerberg", and "the person who started Facebook" all refer to the same entity, whose presence in the text can be detected. In accordance with the present invention, this analysis is used by the computing system to detect certain entities the user is mentioning during an intervention.

For example, in a new exercise, a user may be asked to describe his or her romantic life. The user may already have multiple named entities stored in the computing system, such as one named entity for his or her boss at work, and another named entity stored for the spouse. These named entities may have been detected and stored in prior sessions. In this exercise, the user provides a response but the computing system detects the entity "boss." As such, rather than moving on to the next prompt in the intervention, the computing system attempts to maximize adherence by encouraging the user to shift the focus back to his or her romantic life and therefore increase the adherence fidelity. An exemplary adherence prompt by the computing system in response to detecting the named entity "boss" in a "romantic life" exercise is:

TABLE 1

| | |
|---|---|
| Computing System | Can you describe a recent romantic dinner you had with your wife? |
| User | John has been giving me so much work these days that I barely have time to think about anything else. |
| Computing System | It sounds like you may be talking about your boss at work. Can you try to focus on your romantic life instead? |

Thereafter, if the "boss" entity is continuously detected, the resulting adherence fidelity score of the intervention will be low.

Additional details of the specifics of this technique are omitted herein for brevity. The below list are exemplary publications that are incorporated herein by reference that further describe this technique: "A survey of named entity recognition and classification" by Nadeau, David & Sekine, Satoshi, *Lingvisticae Investigationes* 30.1 (2007): 3-26; "Introduction to the CoNLL-2003 shared task: Language-independent named entity recognition" by Tjong Kim Sang, E. F. & De Meulder, F., *Proceedings of the seventh conference on Natural language learning at HLT-NAACL*, Volume 4, pp. 142-147 (2003); and Wikipedia: https://en.wikipedia.org/wiki/Named-entity_recognition.

II. Text Pattern Matching

The processing units of the one or more sensors described herein may also perform "Text Pattern Matching" analysis, which refers to the ability to detect presence of certain patterns of strings in a body of text (sequences of characters) by matching these patterns to given text. The patterns are typically provided using regular expressions. For example, the pattern "*b*" matches all strings of any length that include the letter "b".

In accordance with the present invention, pattern matching can be used by the computing system to detect certain words or phrases that indicate either an increased or decreased adherence fidelity to the intended implementation of the intervention. For example, pattern matching can be used to detect derogatory and negative words in a gratitude intervention, where the intended implementation is to have a positive and relaxed tone. When detected, the user is guided to try to use a more positive tone and refrain from using this language, so that the adherence fidelity score increases.

Additional details of the specifics of this technique are omitted herein for brevity. The below list are exemplary publications that are incorporated herein by reference that further describe this technique: "Fast pattern matching in strings" by Knuth, Donald E., James H. Morris, Jr, and Vaughan R. Pratt, *SIAM journal on computing* 6.2 (1977): 323-350; "Fast pattern matching in strings" by Knuth, D. E., Morris, Jr., J. H. & Pratt, V. R., *SIAM journal on computing*, 6(2), 323-350 (1977); "Flexible pattern matching in strings: practical on-line search algorithms for texts and biological sequences" by Navarro, G. & Raffinot, M., Cambridge University Press, 2002; and Wikipedia: https://en.wikipedia.org/wiki/Pattern_matching.

III. Sentiment Analysis and Emotional Tone

Sentiment analysis is another technique that may be carried out by the sensors. Basic sentiment analysis identifies the polarity of sentiment in the text between "negative" and "positive." More advanced sentiment analysis provides the ability to identify specific emotions such as "sad" and "angry" and "happy" in a body of text. Furthermore, sentiment analyses of text can identify which segments in the text (i.e. specific words) are indicative of the emotions that were detected. When the conversation is conducted via voice rather than written text, the emotional tone of the text can be further identified by recognizing acoustic characteristics associated with different emotions.

In accordance with a certain intervention of the present invention, the user is asked to describe a negative thought that troubles them. The user responds with a positive thought, which is detected under sentiment analysis as an indication of low adherence fidelity. The computing system then responds trying to guide the user to think of a negative thought that they would like to address and conquer, instead of a positive one. If the user eventually fails to adhere, the adherence score of the intervention remains low upon its completion.

Additional details of the specifics of this technique are omitted herein for brevity. The below list are exemplary publications that are incorporated herein by reference that further describe this technique: "Opinion mining and sentiment analysis" by Pang, Bo, and Lillian Lee, *Foundations and Trends® in Information Retrieval* 2.1-2 (2008): 1-135; "Survey on speech emotion recognition: Features, classification schemes, and databases" by El Ayadi, Moataz, Mohamed S. Kamel, and Fakhri Karray, *Pattern Recognition* 44.3 (2011): 572-587; "Analysis of emotion recognition using facial expressions, speech and multimodal information" by Busso, Carlos, et al., *Proceedings of the 6th international conference on Multimodal interfaces*. ACM, 2004; Google: https://cloud.google.com/natural-language/;

IBM Watson: https://cloud.google.com/natural-language/ & https://www.ibm.com/watson/developercloud/tone-analyzer.html; Microsoft: https://www.microsoft.com/reallifecode/2015/11/29/emotion-detection-and-recognition-from-text-using-deep-learning; and Wikipedia: https://en.wikipedia.org/wiki/Sentiment analysis.

IV. Semantic Analysis

The "Semantic Analysis" refers to various abilities of relating words, phrases, sentences, and paragraphs, to the level of an entire body of text. The sensors in accordance with the present invention can use semantic analysis to assess adherence fidelity. For example, a certain intervention may ask a user to describe a challenge he/she is facing at work. Using a Latent Dirichlet Allocation topic model that was pre-trained on other text data, the computing system identifies that user is discussing two primary topics: "vacation and leisure travel" and "summer." The computing system therefore concludes that the user is describing a summer vacation experience instead of a work challenge, and asks the user to focus on work challenges, so that the user is more faithful to the intended implementation of the intervention.

Additional examples of semantic analyses include: "Part-of-speech tagging" by Voutilainen, Atro, *The Oxford handbook of computational linguistics* (2003): 219-232; "Latent Semantic Analysis" by Landauer, Thomas K, John Wiley & Sons, Ltd, 2006; and "Latent dirichlet allocation" by Blei, David M., Andrew Y. Ng, and Michael I. Jordan, *Journal of machine Learning research* 3. January (2003): 993-1022. Each of the above publications are incorporated herein by reference in its entirety.

V. Natural Language Classification

The "Natural Language Classification" technique assigns text into one of a finite number of categories. The categories are generally defined by labels, and it is possible to decide which labels to use. An exemplary use of this technique in accordance with the present invention to detect the degree of adherence that the user exhibits to the intended implementation is as follows.

TABLE 2

| | |
|---|---|
| Computing System | Can you describe one thing that someone close to you have been struggling with recently? |
| User | I think that Joe does not like me. |
| Computing System | Rather than looking at this from your perspective, can you try and describe things from Joe's perspective? |

In this example, a user is asked to focus on a different person and exhibit empathy towards them. The Natural Language Classifier has been pre-trained to classify between two classes: 1) Self-focus (the writer is focusing on themselves); and 2) Other-focus (the writer is focusing on someone else). The user responded with "I think that Joe does not like me" and when this text is sent to the classifier, the classifier returns the label "Self-focus" indicating that the user is not focused on the other person, resulting in low adherence fidelity. The system then responds in an attempt to increase adherence fidelity by encouraging the user to describe things from the other person's perspective.

Additional details of the specifics of this technique are omitted herein for brevity. The below list are exemplary publications that are incorporated herein by reference that describe this technique: IBM Watson: https://www.ibm.com/watson/developercloud/nl-classifier.html; "Mallet text classification software" http://mallet.cs.umass.edu/classification.php; "A survey of text classification algorithms" by Aggarwal, Charu C., and ChengXiang Zhai, *Mining text data* (2012): 163-222; and Wikipedia:

https://en.wikipedia.org/wiki/Document_classification.

The foregoing list of analytic techniques is not exhaustive but mere examples. An exemplary embodiment may also use other unsupervised analytic techniques, such as topic modeling, to extract potential labels for text classification. Any one of the techniques disclosed herein may be performed by the processing units within the respective sensors or, in the alternative, they may be carried out within one or more processing units external to the respective sensors.

Figure 3:
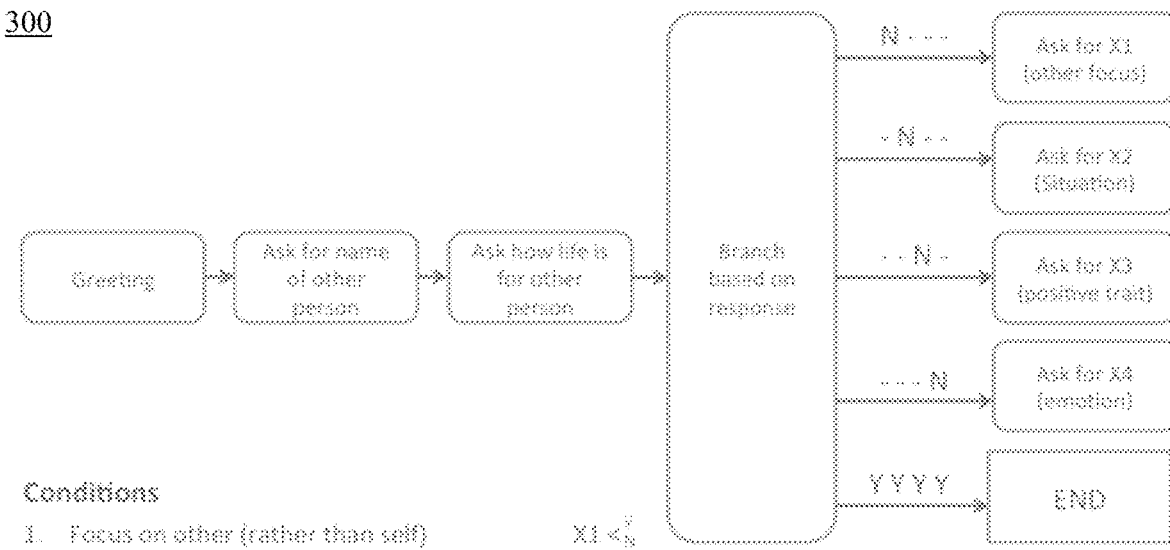
FIG. 3 is an exemplary schematic illustration of a branching logic for an empathy exercise in accordance with the present invention.

An example will now be described with reference to FIG. 3 in which a computing system in accordance with the present invention commences an empathy behavior intervention with a user. This intervention has the intended implementation of having the user "walk in another person's shoes." An exemplary conversation is carried out as follows:

TABLE 3

| | |
|---|---|
| Computing System | Hi John! |
| | Think of a person you know, what is the person's name? |
| User | Joe. |
| Computing System | Thank you. |
| | |
| Computing System | What can you say about Joe's situation? |
| | About how Joe feels, and the way he handles things? |

To accomplish the intended implementation, this particular intervention requires adherence to the following four requirements or conditions:

1) Focusing on another person rather than focusing on oneself.

2) Describing a situation in the other person's life, along with the life domain of this situation (for example, the situation is "dealing with diabetes" where the life domain is "health").

3) Mentioning at least one positive trait of the other person.

4) Describing emotions that the other person is experiencing.

All of these requirements are relevant to the goal of demonstrating empathy and the efficacy of the intervention is maximized when all of them are met. Therefore, upon completion of each of these four requirements, the user receives, for example, a partial score of 25 points. If all four requirements are met the user receives a perfect score of 100. Each step of the intervention may be scored, and these scores may be presented to the user in an individualized fidelity report or an overall fidelity report at the end of the intervention. The presentation of the fidelity reports to the user serves an important purpose of enlightening the user as to why some interventions work or don't work, or why some interventions worked better than others, and/or how the user can improve efficacy of a given intervention. As shown in FIG. 3, when one or more of these conditions are met, the computing system, for example, assigns a "Y" and when one or more of these conditions are missing, the computing system, for example, assigns an "N" or a "-". In this example, an ideal response is assigned [YYYY].

Returning to this example, the conversation is further carried out as follows:

TABLE 4

| | |
|---|---|
| Computing System | Hi John! |
| Computing System | Think of a person you know, what is the person's name? |
| User | Joe. |
| Computing System | Thank you. |
| Computing System | What can you say about Joe's situation? About how Joe feels, and the way he handles things? |
| User | I am a nice person. |
| Computing System | Try to focus on things from Joe's perspective. What is Joe's situation, virtues and emotions? |
| User | Joe is a resilient individual who is dealing with a heavy workload and feeling sad about it. |
| Computing System | Thank you for walking in Joe's shoes! |

The user's first response ("Joe") is analyzed against the programmed branching logic and is assigned [YNNN] because the computing system has detected only the first of the four conditions. The computing system ascertains that there are more conditions to be satisfied and the conversation continues. The user's second response ("I am a nice person") is analyzed and assigned [NNNN] because none of the four conditions has been detected. The computing system ascertains that there are still more conditions to be satisfied and also that the user is deviating off the topic. The computing system responds in a way to bring the user back on track. Finally, the user's third response ("Joe is a resilient individual who is dealing with heavy workload and feeling sad about it") is analyzed and assigned [YYYY] since all four of the conditions have been detected ("Joe", "resilient", "heavy workload" and "feeling sad"). The computing system ascertains that all conditions of the intervention have been met and ends the conversation.

In accordance with the present invention, it is more than merely asking a bunch of different questions in sequence until the user arrives at full adherence. On the contrary, the present invention is, in essence, tailoring each subsequent prompt specifically to guide the user toward achieving the maximized adherence. In other words, at each step of the intervention, the computing system assesses the user provided (e.g., text) input data and based on the assessment, tailors the next prompt accordingly to direct the user toward the maximized adherence. As such, this next prompt may override, or gets assigned a priority over, a pre-arranged next-in-line prompt in accordance with the behavior intervention.

In some embodiments, the programming logic of the intervention is initially designed such that the computing system performs on each input a branching logic such as, for example, when "A"→go to "X," when "B"→go to "Y," when "C"→go to "Z," etc. However, in accordance with the present invention, the computing system may also look into a degree or an amount of how "A" or "B" or "C" is performed rather than simply detecting occurrences of "A" or "B" or "C." As such, the computing system may, instead of branching to "X" or "Y" or "Z" directly, guide the user in a direction that will first maximize adherence to "A" or "B" or "C" of the behavior intervention.

Returning to the empathy behavior intervention example, in the portion of the intervention that requires the user to list a positive trait of the other person, the computing system parses the statement entered by the user to determine whether such statement contains terms that fall into the category of "positive traits." The computing system runs, for example, semantic analysis (e.g., LDA topic modeling) on the entire database's user text for empathy exercises and identifies terms that people have used to describe other people's positive traits. For instance, the terms "smart", "resilient" and "kind" have often been identified as describing positive traits. The identified terms are then used as labels to train a natural language classifier that will identify whether given text can be classified to one of these three identified classes. In accordance with the one or more of the foregoing exemplary analytic techniques, phrases such as "he is smart", "she is clever" or "this is a very intelligent person" may be added to the label identifying the class "smart." For additional details on LDA topic modeling, see "Latent dirichlet allocation" by Blei, D. M., Ng, A. Y. & Jordan, M. I., *Journal of Machine Learning Research,* 3 (January), 993-1022 (2003) and for additional details on general topic modeling, see "Probabilistic Topic Models" by Steyvers, M. & Griffiths, T., *Handbook of Latent Semantic Analysis,* 427(7), 424-440 (2007). Each of these references is herein incorporated by reference in its respective entirety.

If the statement entered by the user fails to contain one or more terms deemed by the computing system to correspond to positive traits of another, then the computing system notifies the user of that failure and asks the user to try again. If the user continuously misses one or more particular conditions of the given intervention, the computing system tailors the follow up prompts to make up for that deficiency. If the user digresses further away from the intended implementation, the computing system appropriately tailors the prompt to get the user back on track. In certain embodiments, the particular tailoring of the prompts in an effort to maximize adherence may be done subtly while in certain other embodiments, the computing system may be more forthright in directing the user toward maximum adherence.

Another exemplary conversation for an empathy behavior intervention is carried out as follows:

TABLE 5

| | |
|---|---|
| Computing System | Hi John! |
| Computing System | Think of a person you know, what is the person's name? |
| User | Max. |
| Computing System | Thank you. |
| Computing System | What can you say about Max's situation? About how Max feels, and the way he handles things? |
| User | Max is a cool guy, but he's been depressed recently. |
| Computing System | Is there a specific situation that Max is dealing with? |
| User | Max is dealing with diabetes. |
| Computing System | Thank you for walking in Max's shoes! |

In this example, the programmed branching logic returns [YNNN] and [YYNY] for the user's first and second responses, respectively. The computing system detects that "other-focus", "positive trait" and "emotion" have been satisfied but that the user has not yet adhered to the "domain" requirement of this intervention. As such, the intervention takes a dynamic turn in the sequence to focus specifically on getting the user toward meeting that missing condition and achieving maximized adherence.

Figure 4:
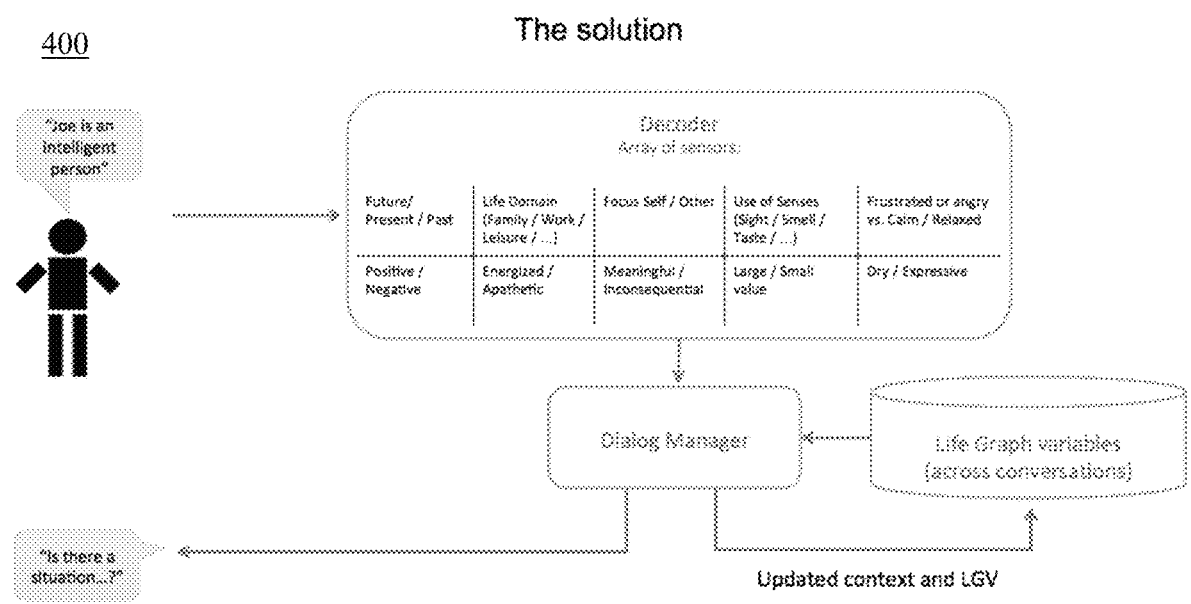
FIG. 4 is an exemplary schematic illustration of a computing system in accordance with the present invention.

Yet another example will be described with reference to FIG. 4. In this example, during a conversation between a computing system and a user, the following steps are depicted:

1) User types or speaks.

2) The text and/or voice signal of the user is "decoded" by a Decoder component of the computing system (i.e., the input data is run through multiple sensors).

3) The result, created and stored by computing the system, is a rich description of the user, providing information such as emotional tone, sentiment, semantics, etc. (e.g., based on the output of one or more sensors described herein).

4) A Dialog Manager then analyzes the sensor outputs, along with the context of the conversation (i.e., representing the interaction with the user in the current conversation) and broader context across conversations, both stored in a repository of context variables.

5) Based on this analysis of the decoded user input and the context, the Dialog Manager then determines how to respond next, and assembles the appropriate response to the user, designed to elicit certain user input in the next turn.

6) The Dialog Manager also updates the repository of context variables (both within and across conversation context variables).

In accordance with an embodiment of the present invention, the Dialog Manager follows the steps above in order to maximize fidelity adherence of the user to the intended implementation of the intervention.

Appearances of the phrase "in an embodiment" or "in an exemplary embodiment," or any other variations of this phrase, appearing in various places throughout the specification are not necessarily all referring to the same embodiment, and only mean that a particular characteristic, feature, structure, and so forth described in connection with the embodiment described is included in at least one embodiment.

The technology described herein may be incorporated in a system, a method, and/or a computer program product, the product including a non-transitory computer readable storage medium having program instructions that are readable by a computer, causing aspects of one or more embodiments to be carried out by a processor. The program instructions are readable by a computer and can be downloaded to a computing/processing device or devices from a computer readable storage medium or to an external computer or external storage device via a network, which can comprise a local or wide area network, a wireless network, or the Internet.

Additionally, the network may comprise wireless transmission, routers, firewalls, switches, copper transmission cables, optical transmission fibers, edge servers, and/or gateway computers. Within the respective computing/processing device, a network adapter card or network interface in each computing/processing device receives computer readable program instructions from the network and forwards the computer readable program instructions for storage in a computer readable storage medium.

As used herein, a computer readable storage medium is not to be construed as being transitory signals, such as radio waves or other freely propagating electromagnetic waves, electromagnetic waves propagating through a waveguide or other transmission media, or electrical signals transmitted through a wire. The computer readable storage medium may be, but is not limited to, e.g., a magnetic storage device, an electronic storage device, an optical storage device, a semiconductor storage device, an electromagnetic storage device, or any suitable combination of the foregoing, and can be a tangible device that can retain and store instructions for use by an instruction execution device. The following is a list of more specific examples of the computer readable storage medium, but is not exhaustive: punch-cards, raised structures in a groove, or other mechanically encoded device having instructions recorded thereon, an erasable programmable read-only memory, a static random access memory, a portable compact disc read-only memory, a digital versatile disk, a portable computer diskette, a hard disk, a random access memory, a read-only memory, flash memory, a memory stick, a floppy disk, and any suitable combination of the foregoing.

The operations of one or more embodiments described herein may be carried out by program instructions which may be machine instructions, machine dependent instructions, microcode, assembler instructions, instruction-set-architecture instructions, firmware instructions, state-setting data, or either source code or object code written in any combination of one or more programming languages, including an object oriented programming language such as, but not limited to, C++, and other conventional procedural programming languages.

The program instructions, as will be clear to those skilled in the art from the context of the description, may have the capability of being executed entirely on a computer of a user, may also be executed partly on the computer of the user, partly on a remote computer and partly on the computer of the user, entirely on the remote computer or server, or as a stand-alone software package. In the "entirely on the remote computer or server" scenario, the remote computer may be connected to the user's computer through any type of network, including a wide area network or a local area network, or the connection may be made to an external computer. In some embodiments, electronic circuitry including, e.g., field-programmable gate arrays, programmable logic circuitry, or programmable logic arrays may execute the program instructions by utilizing state information of the program instructions to personalize the electronic circuitry, in order to perform aspects of one or more of the embodiments described herein. These program instructions may be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. These program instructions may also be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer readable program instructions may also be loaded onto a computer, other programming apparatus, or other device to produce a computer implemented process, such that the instructions which execute on the computer, other programmable apparatus, or other device implement the functions/acts specified in the flowchart and/or block diagram block or blocks.

The block and/or other diagrams and/or flowchart illustrations in the Figures are illustrative of the functionality, architecture, and operation of possible implementations of systems, methods, and computer program products according to the present invention's various embodiments. In this regard, each block in the block and/or other diagrams and/or flowchart illustrations may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently or sometimes in reverse order, depending upon the functionality involved. It will also be noted that each block of the block and/or other diagram and/or flowchart illustration, and combinations of blocks in the block and/or other diagram and/or flowchart illustration, can be implemented by special purpose hardware-based systems that perform the specified functions or acts or carry out combinations of special purpose hardware and computer instructions.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. To aid the Patent Office and any readers of any patent issued on this application in interpreting the claims appended hereto, applicant wish to note that applicant does not intend any of the appended claims or claim elements to invoke 35 U.S.C. § 112(f) unless the words "means for" or "step for" are explicitly used in the particular claim.

In view of the foregoing disclosure, an inventive computing system and technique for interacting with users have been described. In accordance with the disclosure provided herein, a computing system engages with users using a behavior intervention, for the purpose of improving levels of happiness, or more broadly, to alleviate or reduce symptoms of mental health conditions such as depression and anxiety, such interaction entailing assessment of adherence fidelity to the behavior intervention by the computing system, to maximize efficiency of the behavior intervention. In further accordance with the disclosure provided herein, the computing system makes assessments of adherence fidelity and dynamically tailors prompts during the behavior intervention to guide the user toward maximized adherence.

What is claimed is:

1. A computing system for interacting with a user, the computing system comprising:
   at least one processor;
   at least one sensor; and
   at least one memory storing executable software which, when executed by the at least one processor, causes the at least one processor to:
      commence, with a user, a behavior intervention designed to cause an increase in emotional well-being of the user, the behavior intervention having a plurality of conditions to be satisfied;
      receive, via the at least one sensor, input data from the user during the behavior intervention;
      perform, during the behavior intervention, on at least a portion of the received input data having text, semantic analysis to identify terms that satisfy the plurality of conditions;
      determine, during the behavior intervention, based on the identified terms, how many of the plurality of conditions are satisfied; and
      assess, during the behavior intervention, based on the determination of how many of the plurality of conditions are satisfied, a level of adherence to the behavior intervention;
   wherein the executable software stored in the at least one memory is adapted to cause the at least one processor to generate a prompt, during the behavior intervention, based on the assessed level of adherence, designed to elicit, from the user, a response specific to satisfying one or more of the plurality of conditions not satisfied and to advance the behavior intervention towards completion; and
   wherein the behavior intervention further includes a programmed branching logic for responding to the received input data, and wherein the executable software stored in the at least one memory is further adapted to cause the at least one processor to, upon:
      (i) a determination that one or more of the plurality of conditions have yet to be satisfied; and
      (ii) generating the prompt designed to elicit, from the user, the response specific to satisfying the one or more of the plurality of conditions not satisfied,
   assign a priority to the generated prompt over a prearranged next-in-line prompt such that the generated prompt overrides the programmed branching logic for responding to the received input data to direct the user toward maximized adherence.

2. The computing system of claim 1, wherein the executable software stored in the at least one memory is further adapted to cause the at least one processor to receive, via the at least one sensor, input data from the user during the behavior intervention to assess a psychological state of the user while simultaneously assessing the level of adherence to the behavior intervention.

3. The computing system of claim 1, wherein the executable software stored in the at least one memory is further adapted to cause the at least one processor to assess, at a plurality of points in time during the behavior intervention, a respective level of adherence to the behavior intervention at the respective point in time.

4. The computing system of claim 3, wherein the executable software stored in the at least one memory is further adapted to cause the at least one processor to generate, at each of the plurality of points in time, a respective fidelity report containing the respective level of adherence to the behavior intervention assessed at the respective point in time during the behavior intervention.

5. The computing system of claim 4, wherein the executable software stored in the at least one memory is further adapted to cause the at least one processor to generate, at the end of the behavior intervention, an overall fidelity report for the behavior intervention based on a plurality of fidelity reports.

6. The computing system of claim 5, further comprising:
   a display,
   wherein the executable software stored in the at least one memory is adapted to cause the at least one processor to display, on the display, at least one of the fidelity report and the overall fidelity report for viewing by the user, and
   wherein the displaying of the at least one of the fidelity report and the overall fidelity report further enables the user to understand reasons behind efficacy of the behavior intervention.

7. The computing system of claim 1, wherein the behavior intervention is designed to cause an increase in level of happiness of the user.

8. The computing system of claim 1, wherein the behavior intervention is an activity from a plurality of activities belonging to a Happiness track selected by the user from a plurality of selectable Happiness tracks, wherein each Happiness track is a distinct course of program designed to cause an increase in level of happiness of the user.

9. The computing system of claim 1, wherein the behavior intervention is designed to cause a change in one or more of the user's behaviors.

10. The computing system of claim 1, wherein the received input data comprises at least one of verbal and text data from the user.

11. The computing system of claim 1, wherein the semantic analysis includes pre-training a natural language classifier based on a database of user input data and the classifier creating one or more labels to be associated with each of the plurality of conditions.

12. The computing system of claim 11, wherein the semantic analysis further includes determining whether the terms identified in the received input data correspond to the one or more labels.

13. A method of interacting with a user by a computing system, the method comprising:
commencing, with the user, a behavior intervention designed to cause an increase in emotional well-being of the user, the behavior intervention having a plurality of conditions to be satisfied;
receiving, via at least one sensor, input data from the user during the behavior intervention;
performing, during the behavior intervention, on at least a portion of the received input data having text, semantic analysis to identify terms that satisfy the plurality of conditions;
determine, during the behavior intervention, based on the identified terms, how many of the plurality of conditions are satisfied;
assessing, during the behavior intervention, based on the determination of how many of the plurality of conditions are satisfied, a level of adherence to the behavior intervention;
generating a prompt, during the behavior intervention, based on the assessed level of adherence, designed to elicit, from the user, a response specific to satisfying one or more of the plurality of conditions not satisfied and to advance level of adherence towards completion;
including in the behavior intervention a programmed branching logic for responding to the received input data; and
assigning, upon (i) a determination that one or more of the plurality of conditions have yet to be satisfied and (ii) generating the prompt designed to elicit, from the user, the response specific to satisfying the one or more of the plurality of conditions not satisfied, a priority to the generated prompt over a prearranged next-in-line prompt such that the generated prompt overrides the programmed branching logic for responding to the received input data to direct the user toward maximized adherence.

14. The method of claim 13, further comprising:
receiving, via the at least one sensor, input data from the user during the behavior intervention to assess a psychological state of the user while simultaneously assessing the level of adherence to the behavior intervention.

15. The method of claim 13, further comprising:
assessing, at a plurality of points in time during the behavior intervention, a respective level of adherence to the behavior intervention at the respective point in time.

16. The method of claim 15, further comprising:
generating, at each of the plurality of points in time, a respective fidelity report containing the respective level of adherence to the behavior intervention assessed at the respective point in time during the behavior intervention.

17. The method of claim 16, further comprising:
generating, at the end of the behavior intervention, an overall fidelity report for the behavior intervention based on a plurality of fidelity reports.

18. The method of claim 17, further comprising:
displaying, on a display, at least one of the fidelity report and the overall fidelity report for viewing by the user, wherein the displaying of the at least one of the fidelity report and the overall fidelity report further enables the user to understand reasons behind efficiency of the behavior intervention.

19. The method of claim 13, wherein the behavior intervention is designed to cause an increase in level of happiness of the user.

20. The method of claim 13, wherein the behavior intervention is an activity from a plurality of activities belonging to a Happiness track selected by the user from a plurality of selectable Happiness tracks, wherein each Happiness track is a distinct course of program designed to cause an increase in level of happiness of the user.

21. The method of claim 13, wherein the behavior intervention is designed to cause a change in one or more of the user's behaviors.

22. The method of claim 13, wherein the received input data comprises at least one of verbal and text data from the user.

23. The method of claim 13, wherein the semantic analysis includes pre-training a natural language classifier based on a database of user input data and the classifier creating one or more labels to be associated with each of the plurality of conditions.

24. The method of claim 23, wherein the semantic analysis further includes determining whether the terms identified in the received input data correspond to the one or more labels.

25. A computing system for interacting with a user, the computing system comprising:
at least one processor;
at least one sensor; and
at least one memory storing executable software which, when executed by the at least one processor, causes the at least one processor to:
commence, with a user, an empathy behavior intervention designed to cause an increase in expressing empathy by the user, the empathy behavior intervention having a plurality of conditions to be satisfied;
receive, via the at least one sensor, input data from the user during the behavior intervention;
perform, during the empathy behavior intervention, on at least a portion of the received input data having text, semantic analysis to identify terms that satisfy the plurality of conditions;
determine, during the behavior intervention, based on the identified terms, how many of the plurality of conditions are satisfied; and assess, during the empathy behavior intervention, based on the determination of how many of the plurality of conditions are satisfied, a level of adherence to the behavior intervention, wherein the executable software stored in the at least one memory is adapted to cause the at least one processor to generate a prompt, during the empathy behavior intervention, based on the assessed level of adherence, designed to elicit, from the user, a response specific to satisfying one or more of the plurality of conditions not satisfied and to advance the empathy behavior intervention towards completion; and wherein the behavior intervention further includes a programmed branching logic for responding to the received input data, and wherein the executable software stored in the at least one memory is further adapted to cause the at least one processor to, upon:

(i) a determination that one or more of the plurality of conditions have yet to be satisfied; and (ii) generating the prompt designed to elicit, from the user, the response specific to satisfying the one or more of the plurality of conditions not satisfied, assign a priority to the generated prompt over a prearranged next-in-line prompt such that the generated prompt overrides the programmed branching logic for responding to the received input data to direct the user toward maximized adherence.

\* \* \* \* \*